(12) United States Patent
Iwase et al.

(10) Patent No.: US 7,670,320 B2
(45) Date of Patent: Mar. 2, 2010

(54) INDWELLING NEEDLE

(75) Inventors: Yoshiharu Iwase, Tatabashi (JP); Yasuhiro Yamaguchi, Tatebayashi (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/902,442

(22) Filed: Sep. 21, 2007

(65) Prior Publication Data
US 2008/0082054 A1    Apr. 3, 2008

(30) Foreign Application Priority Data
Sep. 21, 2006  (JP) .............................. 2006-256093

(51) Int. Cl.
*A61M 5/32*  (2006.01)
(52) U.S. Cl. ................... 604/198; 604/192; 604/164.01
(58) Field of Classification Search ............ 604/164.01, 604/171, 198, 193, 194, 192
See application file for complete search history.

(56) References Cited
U.S. PATENT DOCUMENTS
5,779,679 A * 7/1998 Shaw .......................... 604/158

6,752,798 B2 *  6/2004  McWethy et al. ............ 604/506
2002/0120215 A1 *  8/2002  Crawford et al. ............ 600/573
2004/0044313 A1 *  3/2004  Nakajima ............... 604/167.02

FOREIGN PATENT DOCUMENTS
JP     A 10-85333       4/1998
JP     A 2002-330945    11/2002
JP     A 2003-180829    7/2003

* cited by examiner

*Primary Examiner*—Kevin C Sirmons
*Assistant Examiner*—Brandy C Scott
(74) *Attorney, Agent, or Firm*—Oliff & Berridge, PLC

(57) ABSTRACT

An indwelling needle includes a cylindrical main body to be fixed to a fitted body, a cylindrical hub for holding a needle, and a cylindrical protective cover which surround the needle and is provided slidably along the needle. In the usage state, the hub and the needle are advanced to the tip end side with respect to the main body and the protective cover is retreated to the rear end side with respect to the main body to project a cutting edge of the needle. In the housed state, the hub is retreated to the rear end side with respect to the main body, and the protective cover is advanced to the tip end side and the cutting edge of the needle is housed within the protective cover. Erroneous sticking into medical staff is prevented, and the burden on a patient is reduced.

11 Claims, 3 Drawing Sheets

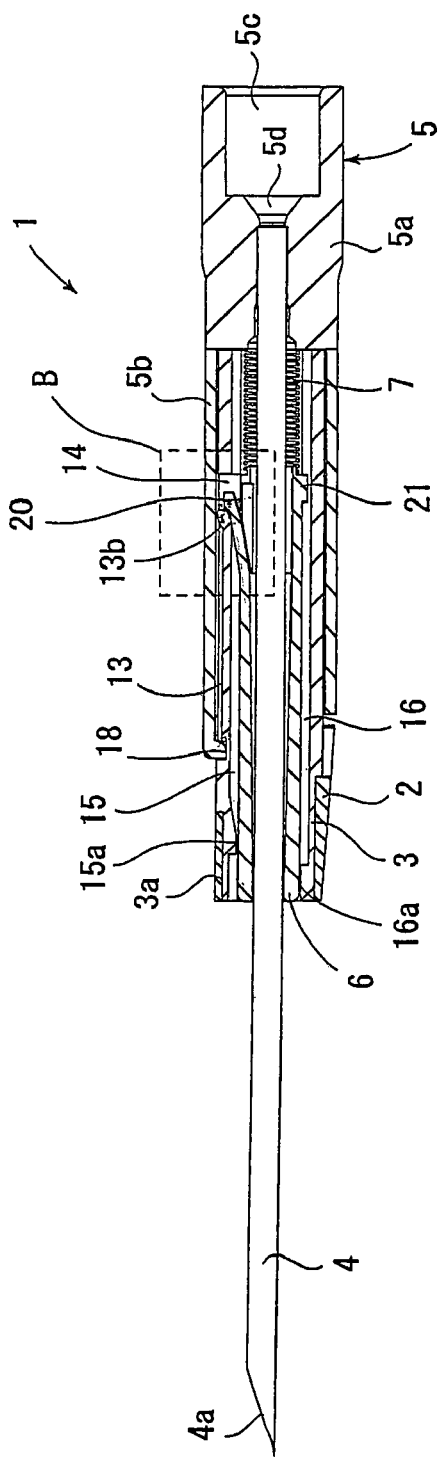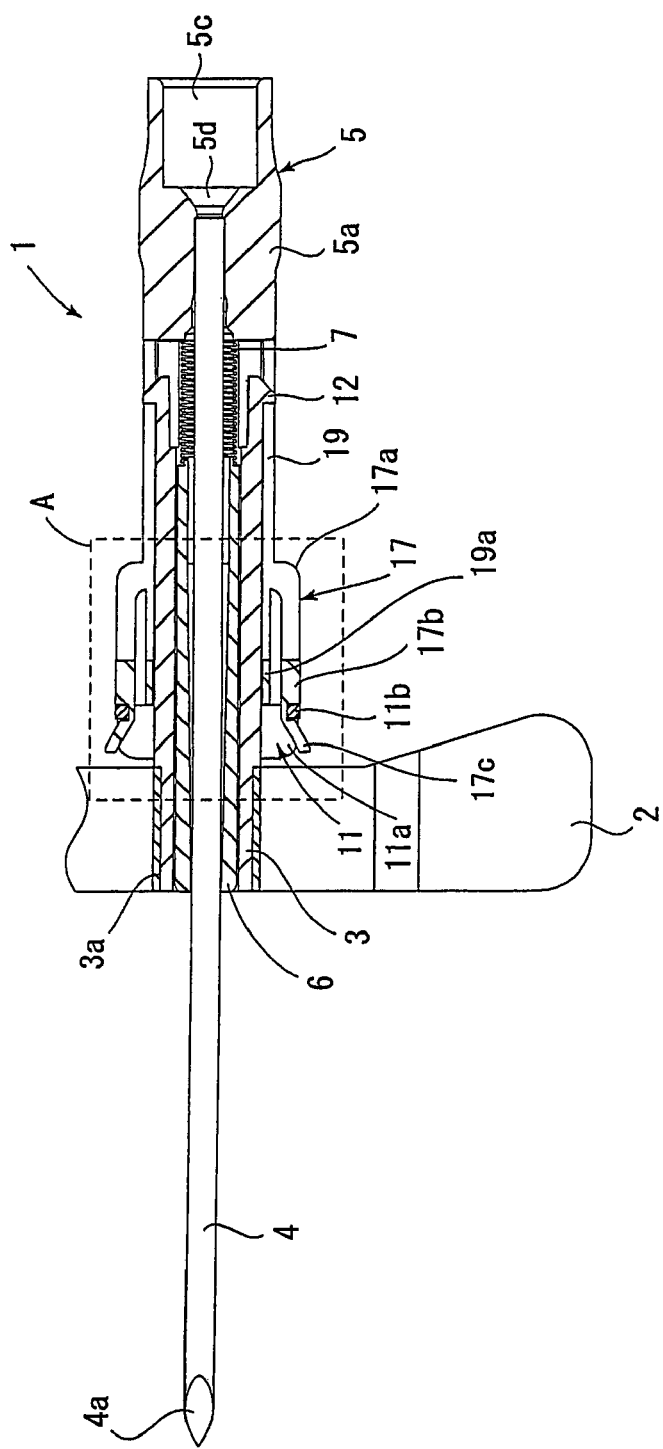
Fig. 2A
Fig. 2B

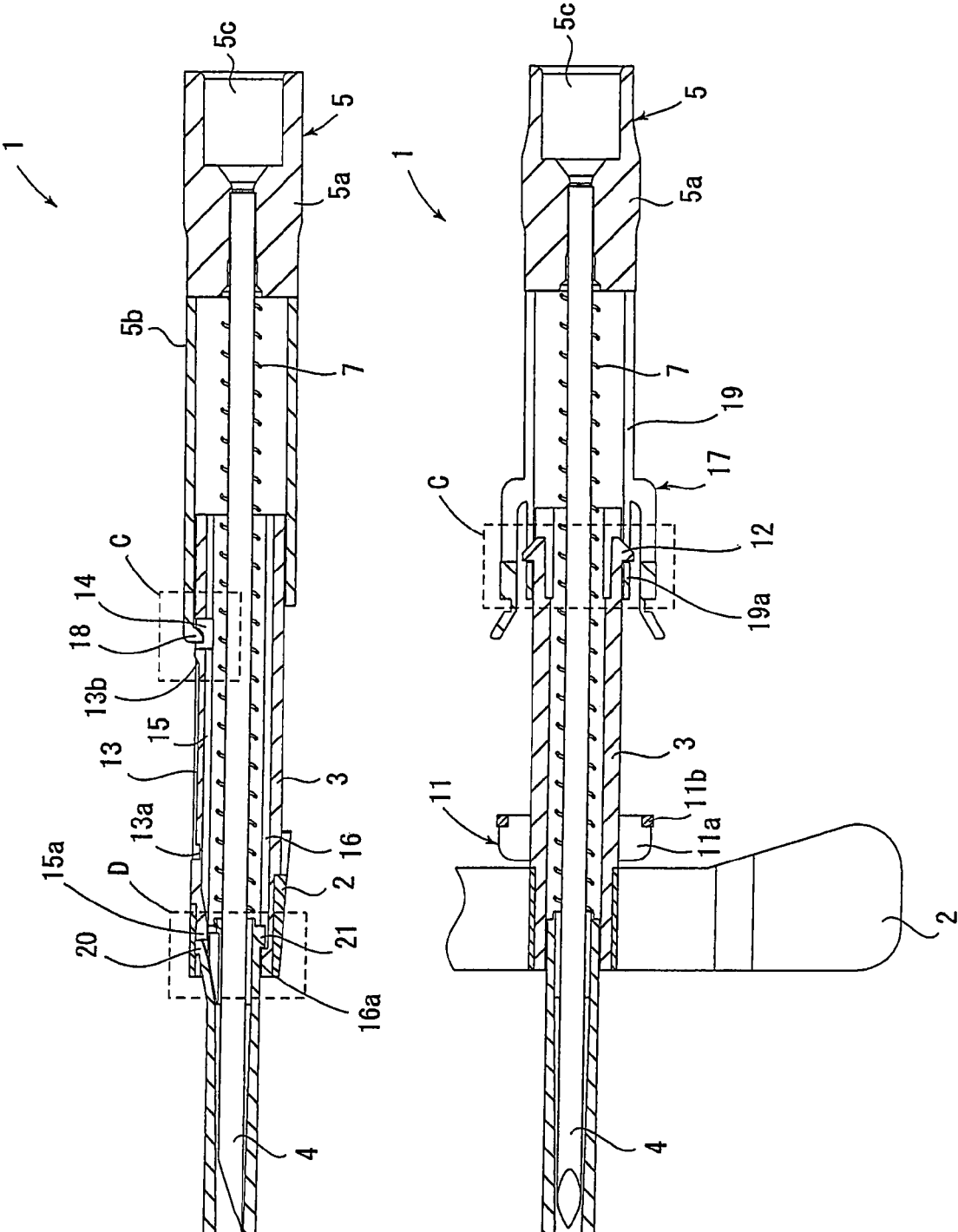

INDWELLING NEEDLE

CROSS-REFERENCE TO RELATED APPLICATION

This application claims priority from Japanese Patent Application No. 2006-256093, filed Sep. 21, 2006. The entire disclosure of which is incorporated by reference in its entirety.

BACKGROUND

The present invention relates to an indwelling needle, more specifically, to an indwelling needle constructed so that a needle is housed within a protective cover in a housed state.

Nowadays, an indwelling needle is inserted into a patient for a drip or dialysis, and in this case, accidents involving erroneously sticking of the indwelling needle pulled out from the patient into medical staff must be prevented.

Therefore, there are known indwelling needles which include a needle having a cutting edge formed on its tip end, a cylindrical hub for holding the rear end of the needle, and a cylindrical protective cover provided so as to advance and retreat along the needle (for example, Japanese Published Unexamined Patent Application No. H10-85333, Japanese Published Unexamined Patent Application No. 2002-330945 and Japanese Published Unexamined Patent Application No. 2003-180829).

The indwelling needle of Patent Application No. H10-85333 is composed of a hub for holding the rear end of a cannula and a holder cylinder which houses and holds the hub inside, and the cannula is housed in the holder cylinder by advancing or retreating the holder cylinder.

The indwelling needle of Patent Application No. 2002-330945 is composed of a hub provided on the rear end of a needle cannula and a safety shield which houses the hub slidably, and when an actuator is operated from a usage state, a spring elastically installed between the hub and the safety shield expands and the safety shield houses the needle cannula.

The indwelling needle of Patent Application No. 2003-180829 is composed of a needle assembly including a needle cannula and a needle hub, and a body which houses the needle assembly in a manner enabling the needle assembly to advance and retreat, and when medical treatment is finished, a sticking element is put into the body due to an elastic force of the spring by operating an operating button.

Thus, according to the indwelling needles of Patent Documents mentioned above, after use, the needle is housed within the protective cover to prevent the above-described accident.

SUMMARY

However, in the case of the above-described indwelling needles, it is necessary to set the length of the protective cover to be longer than the projecting length of the needle from the protective cover, and it is inevitable to make the member to be fixed to the patient in a usage state long.

In the case of a patient, for example, who is subjected to dialysis, tissue of a portion into which a needle is repeatedly stuck becomes hard and forms a knobby swelling. If the length of the member to be fixed to the patient in a usage state is long, when an indwelling needle is fixed to the patient, in some cases, the patient complains of pain because the indwelling needle comes into contact with the swelling and the angle of the needle to be inserted into the blood vessel changes.

In view of such a problem, the present invention provides an indwelling needle which prevents an accident of erroneously sticking a needle into medical staff and whose member to be fixed to a fitted body in a usage state is short in length.

That is, the indwelling needle of claim 1 includes a needle having a cutting edge formed on its tip end; a cylindrical hub for holding the needle; and a cylindrical protective cover provided so as to surround the needle and be slidable along the needle, said cylindrical protective cover being switchable between a usage state that the protective cover is relatively moved to the rear end side of the needle to project the cutting edge of the needle from the protective cover, and a housed state that the protective cover is relatively moved to the tip end side of the needle to house the cutting edge of the needle inside, said indwelling needle further comprising: a fitted body; and a cylindrical main body to be fixed to the fitted body, said hub being slidably provided on the main body so as to be capable of projecting rearward of the main body, said protective cover being slidably provided on the main body so as to be capable of projecting forward of the main body, wherein in the usage state, the hub and the needle are advanced to the tip end side with respect to the main body and the protective cover is retreated to the rear end side with respect to the main body to project the cutting edge of the needle from the protective cover, and in the housed state, the hub is retreated to the rear end side with respect to the main body and the protective cover is advanced to the tip end side to house the cutting edge of the needle within the protective cover.

According to the invention of claim 1, by making a housed state, the needle can be housed within the protective cover, and an accident of erroneously sticking a needle into medical staff can be prevented.

On the other hand, in a usage state, because the protective cover and the hub are made close to each other, the length of the member to be fixed to a fitted body can be shortened in the usage state, and the burden on the patient can be reduced.

In detail, the protective cover and the hub are held slidably by the main body, and in the usage state, the hub is held at a position close to the protective cover side with respect to the main body.

When operating levers are operated from this state to house the indwelling needle, the hub relatively moves away from the main body, and the length of the member that comes into contact with the patient increases by the distance of the relative movement of the hub and the main body.

In other words, in a usage state that the needle is projected to be stuck into the patient, the length of the member that comes into contact with the patient can be reduced by the distance of the relative movement of the hub and the main body, and it becomes possible to fix the indwelling needle while avoiding the swelling appearing on the skin, so that the burden on the patient can be reduced.

BRIEF DESCRIPTION OF THE DRAWINGS

The exemplary embodiment will be described with reference to the drawings, wherein:

FIG. 2A is a sectional view observed from a side surface direction, and FIG. 2B is a sectional view observed from a plain surface direction, both showing a usage state of the indwelling needle; and FIG. 3A is a sectional view observed from a side surface direction, and FIG. 3B is a sectional view observed from a plain surface direction, both showing a housed state of the indwelling needle.

DETAILED DESCRIPTION OF EMBODIMENTS

Figure 1:
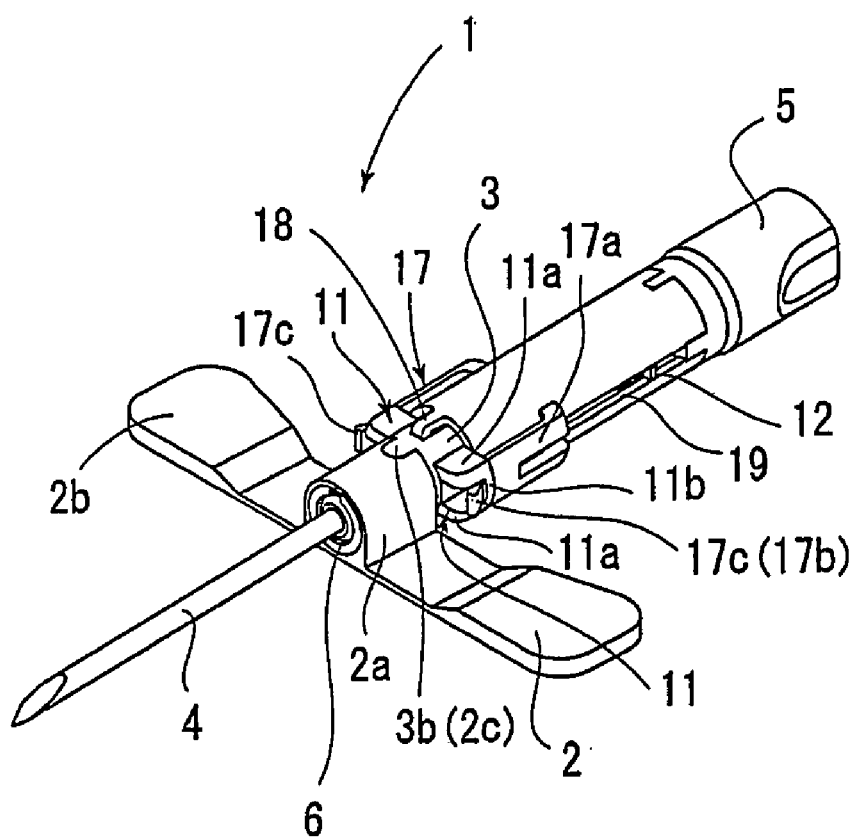
FIG. 1 is a perspective view of the housed state of the indwelling needle of this embodiment.

Hereinafter, an embodiment of the present invention will be described. FIGS. 1 through 3 show an indwelling needle 1 according to the present invention, and among these drawings, FIG. 1 is a perspective view of the indwelling needle 1 in a usage state, FIG. 2 are sectional views of the indwelling needle 1 in the usage state, and FIG. 3 are sectional views of the same in a housed state.

FIG. 2A and FIG. 3A are sectional views from a side surface of the indwelling needle 1, FIG. 2B and FIG. 3B are sectional views of the indwelling needle 1 from a plan view direction. In the following description, the side of a cutting edge 4a of the needle 4 is defined as a tip end side of the indwelling needle 1, the up and down direction of the illustration of FIG. 2A is defined as the up and down direction of the indwelling needle 1, and the up and down direction of the illustration of FIG. 2B is defined as a side surface of the indwelling needle 1.

The indwelling needle 1 of the embodiment is composed of a wing-like member 2 to be fixed to a patient as a fitted body, a cylindrical main body 3 to be fixed to the patient via the wing-like member 2, a hollow needle 4 having a cutting edge 4a on its tip end, a cylindrical hub 5 which holds the rear end of the needle 4 and slidably moves at the rear end side of the main body 3, a cylindrical protective cover 6 which slidably moves at the tip end side of the main body 3, and a spring 7 elastically installed between the hub 5 and the protective cover 6.

The usage state of the indwelling needle 1 means a state that the hub 5 and the needle 4 are advanced to the tip end side with respect to the main body 3 and the protective cover 6 is retreated to the rear end side with respect to the main body 3 to project the cutting edge 4a of the needle 4 from the protective cover 6. In the usage state, the cutting edge 4a of the needle 4 is stuck into a patient and the main body 3 is fixed together with the wing-like member 2 to a patient with an adhesive tape, etc.

On the other hand, the housed state of the indwelling needle 1 means a state that the hub 5 is retreated to the rear end side with respect to the main body 3 and the protective cover 6 is advanced to the tip end side to house the cutting edge 4a of the needle 4 within the protective cover 6. When transfusion to a patient, etc., is finished, the needle 4 is housed within the protective cover 6, whereby an accident of sticking of the cutting edge 4a into medical staff is prevented.

The indwelling needle 1 of this embodiment is provided with a first maintaining mechanism A which maintains the main body 3 and the hub 5 in the usage state, a second maintaining mechanism B which maintains the main body 3 and the protective cover 6 in the usage state, a third maintaining mechanism C which maintains the main body 3 and the hub 5 in the housed state, and a fourth maintaining mechanism D which maintains the main body 3 and the protective cover 6 in the housed state.

The wing-like member 2 is composed of a cylindrical portion 2a surrounding the main body 3, and wings 2b spreading to both sides of the cylindrical portion 2a, and a groove 2c for preventing rotation is formed on the upper side of the cylindrical portion 2a.

The wings 2b are deformed along the skin of a patient and fixed with an adhesive tape, etc., from the surface of the wing-like member 2, whereby the indwelling needle 1 is fixed to the patient.

The main body 3, having a substantially cylindrical shape, is held slidably inside the hub 5, and houses the protective cover 6 inside to hold it slidably.

On the tip end of the main body 3, a connecting portion 3a in which the cylindrical portion 2a of the wing-like member 2 fits is formed, and on the upper side of the connecting portion 3a, a convex form 3b which fits in the groove 2c of the cylindrical portion 2a is formed to prevent relative rotations of the wing-like member 2 and the main body 3.

As shown in FIG. 3B, engaging means 11 are provided on the front sides of both side surfaces of the main body 3, and on the rear sides, third engaging portions 12 projecting toward the hub 5 are formed.

As shown in FIG. 1, the engaging means 11 is composed of a pair of plate members 11a and rod-like first engaged portions 11b laid across the two plate members 11a.

As shown in FIG. 3A, in the upper portion of the outer peripheral surface of the main body 3, a first guide groove 13 is formed in the front and rear direction, and at the tip end and rear end of the first guide groove 13, concave portions 13a and inclined surfaces 13b are formed, respectively. Behind the first guide groove 13, a through hole 14 as a second engaged portion and a fourth engaged portion is opened.

Furthermore, a second guide groove 15 is formed in the upper portion of the inner peripheral surface of the main body 3 from the tip end to the rear end, and a third guide groove 16 is formed in the lower portion thereof from the tip end to the rear end.

A sixth engaged portion 15a and a fifth engaged portion 16a project toward the inner peripheral side at the front sides of these second guide groove 15 and the third guide groove 16. The fifth engaged portion 16a is positioned at the tip end of the main body 3. The sixth engaged portion 15a is positioned slightly rear of the fifth engaged portion 16a, and furthermore, provided with an inclined surface in the rear of the sixth engaged portion 15a.

The hub 5 is composed of a holder 5a for holding the needle 4, a cylindrical portion 5b for housing the main body 3, and a connecting portion 5c to which a transfusion tube (not shown) is connected. The holder 5a and the cylindrical portion 5b are made respectively as a separate member.

The holder 5a fits and holds the rear end of the needle 4, and the rear end of the spring 7 comes into elastic contact with the tip end of the holder so as to surround the needle 4. In the usage state, the rear end of the main body 3 comes into contact with the holder so as to surround the spring 7.

Furthermore, a liquid channel 5d is formed between the holder 5a and the connecting portion 5c, and an infusion fluid flowing-in via the transfusion tube is supplied to the needle 4 through the liquid channel 5d.

The cylindrical portion 5b comes into contact at its tip end with the rear ends of the plate members 11a of the engaging means 11 of the main body 3 in the usage state, and operating levers 17 are provided on both side surfaces of the cylindrical portion 5b.

The operating lever 17 is composed of an arm 17a having flexibility whose rear end is fixed to the cylindrical portion 5b and a first engaging portion 17b provided at the tip end of the arm 17a.

Concave portions are formed on the first engaging portions 17b toward the outer peripheral side, and in the usage state, the first engaged portions 11b provided on the engaging means 11 of the main body 3 are housed inside the concave portions so as to engage with each other.

Knobs 17c are formed on the tip ends of the first engaging portions 17b. The arms 17a are elastically deformed by pressing the knobs from both sides to release the engagements of the first engaging portions 17b with the first engaged portions 11b.

On the upper portion of the cylindrical portion 5b, a first projection 18 as a pressing member and a fourth engaging portion projecting toward the main body 3 is formed, and the first projection 18 is formed at the tip end of a rod-like member having flexibility and projecting forward from the tip end of the cylindrical portion 5b.

The first projection 18 is housed in the concave portion 13a of the first guide groove 13 in the usage state, and retreats along the first guide groove 13 according to retreat of the hub 5. When the first projection 18 gets over the inclined surface 13b formed at the rear end of the first guide groove 13, it is housed inside the through hole 14.

Furthermore, on both side surfaces of the cylindrical portion 5b, fourth guide grooves 19 are formed in the front and rear direction, and the fourth guide grooves 19 are formed to the middles of the arms 17a of the operating levers 17, and at the tip ends thereof, third engaged portions 19a in which the third engaging portions 12 of the main body 3 come into contact with are formed.

Next, the protective cover 6 is housed slidably inside the main body 3 so that its tip end comes to the same position as that of the tip end of the main body 3 in the usage state, and with the rear end of the protective cover, the spring 7 is in elastic contact.

On the upper portion of the protective cover 6, a second projection 20 as a second engaging portion and a sixth engaging portion which moves along the second guide groove 15 of the main body 3 is formed, and on the lower portion of the protective cover 6, a fifth engaging portion 21 which moves along the third guide groove 16 of the main body 3 projects.

The second projection 20 is formed on the rear end of a rod-like member inclined from the tip end side toward the rear end side, and engages with the through hole 14 formed in the main body 3 in the usage state.

When the engagement with the through hole 14 is released, the second projection 20 advances in association with the protective cover 6, and gets over the inclined surface of the sixth engaged portion 15a formed in the second guide groove 15 and the rear end face of the second projection 20 and the tip end face of the sixth engaged portion 15a engage with each other.

On the other hand, the fifth engaging portion 21 also advances in association with the protective cover 6, and when the protective cover 6 reaches the position of the housed state, the tip end face of the fifth engaging portion 21 and the rear end face of the fifth engaged portion 16a formed in the third guide groove 16 come into contact with each other to engage with each other.

Because the second projection 20 and the fifth engaging portion 21 engage with the second and third guide grooves 15 and 16, respectively, the protective cover 6 and the main body 3 are prevented from relatively rotating.

Hereinafter, first through fourth maintaining mechanisms A through D which maintain the indwelling needle 1 in the usage state and the housed state will be described. First, the first maintaining mechanism A which maintains the main body 3 and the hub 5 in the usage state will be described.

As shown in FIG. 2B, the first maintaining mechanism A is composed of engaging means 11 provided on the main body 3 and operating levers 17 provided on the hub 5.

In detail, the rear end faces of the first engaging portions 17b engages with the tip end faces of the first engaged portions 11b by housing the first engaged portions 11b provided on the engaging means 11 within the concave portions formed on the first engaging portions 17b of the operating levers 17, thereby the usage state is maintained where the main body 3 and the hub 5 come close to each other against the elastic force of the spring 7.

Then, in order to release the first maintaining mechanism A, it is only required to press the knobs 17c of the operating levers 17 from both sides toward the main body 3 side, thereby, when the engagements of the first engaging portions 17b with the first engaged portions 11b are released, the main body 3 and the hub 5 are spaced from each other due to the elastic force of the spring 7. At this time, the first engaging portions 17b pass through between the first engaged portions 11b and the surface of the main body 3.

Next, a second maintaining mechanism B which maintains the main body 3 and the protective cover 6 in the usage state will be described.

As shown in FIG. 2A, the second maintaining mechanism B is composed of a second projection 20 as a second engaging portion provided on the upper portion of the protective cover 6 and a through hole 14 as a second engaged portion formed in the main body 3.

In detail, by housing the second projection 20 in the through hole 14, the state is maintained where the main body 3 and the protective cover 6 come close to each other against the elastic force of the spring 7.

The second maintaining mechanism B is released by a releasing mechanism, which is the first projection 18 as a pressing member provided on the hub 5 in the present embodiment.

As described below, the first maintaining mechanism A is released and the hub 5 retreats with respect to the main body 3. The hub 5 and the main body 3 are maintained in the housed state, and at the same time, the first projection 18 formed on the hub 5 is housed in the through hole 14.

At this time, the first projection 18 returns to the inner peripheral side of the main body 3 by getting over the inclined surface 13b of the first guide groove 13, and due to this force, the first projection 18 comes into contact with the second projection 20 and presses the second projection 20 to the inner peripheral side of the main body 3.

As a result, the engagement of the second projection 20 with the through hole 14 is released, thereby the main body 3 and the protective cover 6 are spaced from each other due to the elastic force of the spring 7.

Next, the third maintaining mechanism C which maintains the main body 3 and the hub 5 in the housed state will be described.

The third maintaining mechanism C is composed of, as shown in FIG. 3(a), the first projection 18 as the fourth engaging portion provided on the hub 5 and the through hole 14 as the fourth engaged portion formed in the main body 3, and as shown in FIG. 3(b), is composed of the third engaging portions 12 provided on the main body 3 and the third engaged portions 19a formed on the hub 5.

As shown in FIG. 3(a), when the first maintaining mechanism A is released to retreat the hub 5 with respect to the main body 3, the first projection 18 provided on the hub 5 comes out from the concave portion 13a of the first guide groove 13 formed in the main body 3 to retreat along the first guide groove 13.

Then, when the first projection 18 gets over the inclined surface 13b of the first guide groove 13 and is housed in the through hole 14, the tip end face of the first projection 18 and the through hole 14 engages with each other.

As a result, the main body 3 and the hub 5 are prevented from approaching each other to prevent the indwelling needle 1 from returning into the usage state again and prevent the cutting edge of the needle 4 from being exposed.

At this time, by housing the first projection 18 in the through hole 14, the first projection 18 presses the second projection 20 to release the engagement with the through hole 14 and release the second maintaining mechanism B.

On the other hand, as shown in FIG. 3B, when the hub 5 retreats with respect to the main body 3, the tip end faces of the third engagement portions 12 provided on the main body 3 and the rear end faces of the third engaged portions 19a formed in the fourth guide grooves 19 of the hub 5 come into contact with each other. As a result, the hub 5 urged rearward by the elastic force of the spring 7 does not retreat further, and the hub 5 can be prevented from coming off the main body 3.

Last, the fourth maintaining mechanism D which maintains the main body 3 and the protective cover 6 in the housed state will be described.

The fourth maintaining mechanism D is composed of, as shown in FIG. 3(1), the second projection 20 as the sixth engaging portion formed on the protective cover 6 and the sixth engaged portion 15a formed in the second guide groove 15 of the main body 3, and is composed of the fifth engaging portion 21 formed on the protective cover 6 and the fifth engaged portion 16a formed in the third guide groove 16.

When the protective cover 6 retreats with respect to the main body 3 according to releasing of the second maintaining mechanism B and the second projection 20 gets over the inclined surface formed on the rear end of the sixth engaged portion 15a, the rear end face of the second projection 20 and the tip end face of the sixth engaged portion 15a engage with each other, and at the same time, the tip end face of the fifth engaging portion 21 comes into contact with the rear end face of the fifth engaged portion 16a to engage with each other.

As a result, the main body 3 and the protective cover 6 are prevented from approaching each other, and the indwelling needle 1 is prevented from returning into the usage state again and the tip end of the needle 4 is prevented from being exposed. Furthermore the protective cover 6 urged forward by the elastic force of the spring 7 does not advance further, and the protective cover 6 is prevented from coming off the main body 3.

A method for using the indwelling needle 1 of this embodiment having the above structure will be described.

First, the indwelling needle 1 is used in the usage state, and a transfusion tube is connected to the connecting portion 5c of the hub 5 in advance, and the outer periphery of the needle 4 is covered by a cover (not shown) until the needle 4 is stuck into the patient.

Next, after the cover is removed and the needle 4 is stuck into a blood vessel of the patient and the wing-like member 2 is deformed along the skin of the patient, the wing-like member 2 is fixed to the patient with tape, etc., thereby the indwelling needle 1 is fixed to the patient.

Thereafter, the infusion fluid from the transfusion tube is infused into the patient via the liquid channel 5d formed in the hub 5 and the needle 4. When the transfusion is finished, first, the tape which fixes the wing-like member 2 is peeled off. Without pulling the needle 4 out of the patient, the knobs 17c of the operating levers 17 are pressed from both sides to release the first maintaining mechanism A.

At this time, because the hub 5 and the protective cover 6 are urged in a direction of spacing from each other, the hub 5 retreats with respect to the main body 3 according to releasing of the first maintaining mechanism A, and on the other hand, because the protective cover 6 is maintained in the usage state by the second maintaining mechanism B, it is prevented from advancing with respect to the main body 3.

When the hub 5 relatively moves to the rear end side with respect to the main body 3, the needle 4 also relatively moves to the rear end side with respect to the main body 3, and the needle 4 is pulled out from the blood vessel of the patient. At this time, it is not always necessary that the needle 4 is completely pulled out from the blood vessel.

When the hub 5 thus retreats with respect to the main body 3, the first projection 18 provided on the tip end of the cylindrical portion 5b also retreats along the first guide groove 13 formed in the main body 3.

Thereafter, the first projection 18 gets over the inclined surface 13b formed on the rear end of the first guide groove 13 to be housed within the through hole 14, whereby the main body 3 and the hub 5 are maintained in the housed state by the third maintaining mechanism C.

The main body 3 and the hub 5 are maintained by the third maintaining mechanism C, and at the same time, the second projection 20 provided on the protective cover 6 is pressed to the inner peripheral side by the first projection 18, and the second maintaining mechanism B is released by releasing means.

When the second maintaining mechanism B is released, the protective cover 6 relatively moves forward due to the elastic force of the spring 7, and the second projection 20 formed on the protective cover 6 and the fifth engaging portion 21 advance along the second and third guide grooves 15 and 16.

The second projection 20 gets over the sixth engaged portion 15a to engage with the sixth engaged portion 15a. on the other hand, the fifth engaging portion 21 and a fifth engaged portion 16a of the third guide groove 16 engage with each other by the advancement of the protective cover 6, whereby the main body 3 and the protective cover 6 are maintained in the housed state by the fourth maintaining mechanism D.

According to the thus structured indwelling needle 1 of this embodiment, by changing the state of the indwelling needle 1 from the usage state into the housed state, the needle 4 is housed within the protective cover 6, and an accident of erroneously sticking of the needle 4 into medical staff can be prevented.

According to the indwelling needle 1 of this embodiment, in the usage state, by positioning the hub 5 at the tip end side with respect to the main body 3, most of the main body 3 is housed within the cylindrical portion 5b, and the length of the member that comes into contact with the patient can be shortened.

By changing into the housed state from this usage state, the hub 5 relatively moves to the rear end side with respect to the main body 3, the main body 3 is exposed from the hub 5 and the portion that comes into contact with a patient is lengthened, however, this housed state continues only in a short period of time that the indwelling needle 1 is pulled out from the patient, and does not impose a burden on the patient.

Furthermore, according to an indwelling needle 1 of this embodiment, when changing from the usage state into the housed state, damage to the blood vessel of the patient can be prevented, and scattering of blood can be prevented.

In detail, in the process of changing the indwelling needle 1 from the usage state into the housed state, when the first maintaining mechanism A is released and the main body 3 and the hub 5 are maintained in the housed state by the third maintaining mechanism C, the second maintaining mechanism B is released by the releasing means.

That is, after the hub 5 retreats with respect to the main body 3, the protective cover 6 advances with respect to the main body 3, so that the protective cover 6 advances after a part of the needle 4 is pulled out, which reduces pain of the patient caused by the contact with the protective cover 6.

After the entirety of the needle 4 is pulled out, scattering of the blood adhering to the inside and surface of the needle 4 can be controlled by advancing of the protective cover 6. Furthermore, the protective cover 6 is maintained in the housed state by the fourth maintaining mechanism D, so that an accident that the needle 4 projects from the protective cover 6 and is stuck into medical staff can be prevented.

What is claimed is:

1. An indwelling needle comprising:
a needle having a cutting edge formed on its tip end;
a cylindrical hub for holding the needle;
a cylindrical protective cover provided so as to surround the needle and be slidable along the needle;
a cylindrical main body to be fixed to a fitted body in which a cutting edge of the needle is inserted, said cylindrical hub being slidably placed along an outer periphery of said cylindrical main body while said cylindrical protective cover is slidably placed along an inner periphery of said cylindrical main body, wherein
said cylindrical protective cover is switchable between a usage state in which the protective cover is relatively moved to a rear end side of said cylindrical main body and said cylindrical hub along together with said needle is relatively moved to a tip end side of said cylindrical main body to project the cutting edge of the needle from the protective cover, and a housed state in which said cylindrical hub together with said needle is relatively moved to the rear end side of said cylindrical main body and the protective cover is relatively moved to the tip end side of said cylindrical main body to house the cutting edge of the needle inside;
a spring by which the cylindrical hub is moved rearward with respect to the cylindrical main body while the protective cover is moved forward with respect to the cylindrical main body such that said usage state is shifted to said housed state;
a first maintaining mechanism provided between the cylindrical main body and the cylindrical hub, by which the cylindrical hub and the needle are latched and released at a position where the cylindrical hub and the needle are advanced with respect to the cylindrical main body by the spring in the usage state;
a second maintaining mechanism provided between the cylindrical main body and the protective cover, by which the cutting edge of the needle is latched and released at a position where the protective cover moves rearward with respect to the cylindrical main body against the spring in the usage state so that the cutting edge of the needle projects further than the protective cover; and
a projection formed on said cylindrical hub such that when said cylindrical hub is moved rearward with respect to said cylindrical main body by releasing an engagement of said first maintaining mechanism in said usage state, the projection facilitates the release of an engagement of said second maintaining mechanism so that said cylindrical protective cover is moved forward with respect to said cylindrical main body,
wherein when an engagement of the first maintaining mechanism is released, in the usage state where the cylindrical main body is fixed to the fitted body with the needle being inserted therein,
the cylindrical hub retreats along with the needle against the spring,
a portion of the needle is removed from the fitted body while an engagement piece of the first maintaining mechanism releases said engagement of the second maintaining mechanism,
the protective cover advances by the spring, and
the cutting edge of the needle is housed in the protective cover.

2. The indwelling needle according to claim 1, wherein:
the spring is elastically installed between the hub and the protective cover,
the first maintaining mechanism maintains the main body and the hub in the usage state against an elastic force of the spring,
the second maintaining mechanism maintains the main body and the protective cover in the usage state against the elastic force of the spring, and the indwelling needle further includes:
a releasing mechanism provided so as to release the second maintaining mechanism when the hub retreats with respect to the main body, wherein:
the first maintaining mechanism is released from the usage state and the hub retreats due to the elastic force of the spring, and then the second maintaining mechanism is released by the releasing mechanism and due to the elastic force of the spring the protective cover advances and makes the housed state.

3. The indwelling needle according to claim 2, wherein the first maintaining mechanism comprising:
flexible arms being fixed to the hub on the one ends,
first engaging portions formed on the other ends of the arms, and
first engaged portions which are provided on the main body and are engaged with the first engaging portions, wherein:
the first engaging portions and the first engaged portions engage with each other in the usage state; and
in order to release the first maintaining mechanism, the arms are deformed to release the engagements between the first engaging portions and the first engaged portions.

4. The indwelling needle according to claim 3, wherein:
when the first maintaining mechanism is released from the usage state, the hub retreats due to the elastic force of the spring; and
when the second maintaining mechanism is released by the releasing mechanism, the protective cover advances due to the elastic force of the spring and makes the housed state.

5. The indwelling needle according to claim 3, wherein:
the protective cover is held slidably inside the main body,
the second maintaining mechanism comprises a second engaging portion projecting to the main body side from the protective cover and a second engaged portion formed on the main body,
the second engaging portion and the second engaged portion engage with each other in the usage state, and
in order to release the second maintaining mechanism, the engagement of the second engaging portion and the second engaged portion is released.

6. The indwelling needle according to claim 5, wherein:
the hub holds the main body slidably,
the second engaged portion in the second maintaining mechanism is a through hole formed in the main body,
the second engaging portion and the through hole engage with each other in the usage state, the releasing mechanism is the projection formed on said cylindrical hub, wherein the projection is a pressing member which projects to the main body side from the hub, and when the first maintaining mechanism is released, the hub retreats with respect to the main body, and the pressing member is housed in the through hole from the outer peripheral side of the main body, then the second engaging portion is pushed to the inner peripheral side by the pressing member so as to release the engagement between the second engaging portion and the through hole.

7. The indwelling needle according to claim 6, comprising:

a third maintaining mechanism which maintains the hub and the main body in the housed state, wherein:

the third maintaining mechanism comprising;

third engaging portions to be formed on either the hub or the main body so as to project to the other and third engaged portions formed on either the hub and the main body so as to be engaged with the engaging portions, and in the housed state, the third engaging portions and the third engaged portions engage with each other to prevent the hub from falling off the main body.

8. The indwelling needle according to claim 7, wherein the third maintaining mechanism further comprising:

a fourth engaging portion to be formed on either the hub or the main body so as to project to the other and a fourth engaged portion to be formed on either the hub and the main body so as to be engaged with the fourth engaging portion, and in the housed state, the fourth engaging portion and the fourth engaged portion engage with each other to prevent return to the usage state.

9. The indwelling needle according to claim 8, comprising:

a fourth maintaining mechanism which maintains the protective cover in the housed state with respect to the main body, wherein:

the fourth maintaining mechanism comprising;

a fifth engaging portion to be formed on either the protective cover or the main body so as to project to the other and a fifth engaged portion to be formed on either the protective cover or the main body so as to be engaged with the fifth engaging portion, and when the protective cover advances with respect to the main body, the fifth engaging portion engages with the fifth engaged portion and turns into the housed state to prevent the protective cover from falling off the main body.

10. The indwelling needle according to claim 9, wherein the fourth maintaining mechanism further comprising:

a sixth engaging portion to be formed on either the protective cover or the main body and a sixth engaged portion to be formed on the other, and when the protective cover advances with respect to the main body, the sixth engaging portion engages with the sixth engaged portion and turns into the housed state to prevent return to the usage state.

11. The indwelling needle according to claim 9, wherein a wing-like member for fixing the main body to the fitted body is provided on the main body.

\* \* \* \* \*